United States Patent [19]

Baker et al.

[11] Patent Number: 5,021,441
[45] Date of Patent: Jun. 4, 1991

[54] ORGANIC COMPOUNDS AND THEIR PHARMACEUTICAL USE

[75] Inventors: Stephen R. Baker, Indianapolis, Ind.; Alec Todd, Workingham, England

[73] Assignee: Lilly Industries Limited, Basingstoke, England

[21] Appl. No.: 326,939

[22] Filed: Mar. 22, 1989

[30] Foreign Application Priority Data

Mar. 24, 1988 [GB] United Kingdom ............... 8807016

[51] Int. Cl.$^5$ .................. A61K 31/41; A61K 31/19; C07D 257/04; C07C 63/14
[52] U.S. Cl. .................. 514/381; 514/570; 548/253; 562/426
[58] Field of Search ............... 548/253; 514/381, 570; 562/426

[56] References Cited

U.S. PATENT DOCUMENTS

| 4,513,005 | 4/1985 | Baker et al. | 514/451 |
| 4,665,189 | 5/1987 | Baker et al. | 548/252 |
| 4,675,335 | 6/1987 | Baker et al. | 514/381 |

FOREIGN PATENT DOCUMENTS

| 123543 | 10/1984 | European Pat. Off. |
| 228045 | 7/1987 | European Pat. Off. |
| 298583 | 1/1989 | European Pat. Off. |
| 2144422 | 3/1985 | United Kingdom |
| 2168704 | 6/1986 | United Kingdom |
| 2170204 | 7/1986 | United Kingdom |

Primary Examiner—David B. Springer
Attorney, Agent, or Firm—Robert A. Conrad; Leroy Whitaker

[57] ABSTRACT

There are disclosed pharmaceutical compounds of the formula:

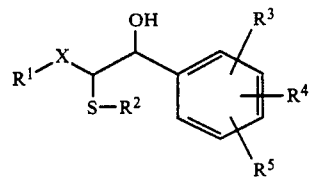

in which
$R^1$ is halo-substituted alkyl;
X is alkenylene; and $R^1$—X— contains 6 to 34 carbon atoms;
$R^2$ is $C_{1-5}$ alkyl substituted by
(i) optionally protected carboxyl, nitrile, optionally protected tetrazolyl or —CONR'R", in which R' and R" are each hydrogen or $C_{1-4}$ alkyl,

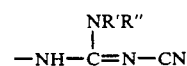

(ii) in which R' and R" are each hydrogen or $C_{1-4}$ alkyl, or

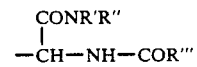

(iii) in which R', R" and R'" are each hydrogen or $C_{1-4}$ alkyl, or
$R^2$ is a group of the formula

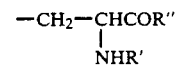

in which R' is hydrogen or an optionally protected amino acid residue, and R" is —OH or an optionally protected amino acid residue; and
$R^3$, $R^4$ and $R^5$ are each hydrogen, optionally protected carboxyl, $C_{1-4}$ alkyl, $C_{1-4}$ alkoxy, hydroxyl, optionally protected tetrazolyl, halo, trifluoromethyl, nitrile, nitro or —CONR'R" where R' and R" are each hydrogen or $C_{1-4}$ alkyl; and salts thereof.

8 Claims, No Drawings

ORGANIC COMPOUNDS AND THEIR PHARMACEUTICAL USE

This invention relates to organic compounds and their use as pharmaceuticals.

A group of thio-substituted aromatic alcohols having the formula

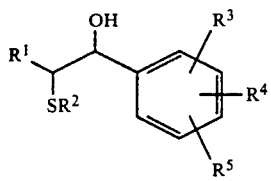

is disclosed in British Patent 2 144 422. These compounds have an antagonist effect on leukotriene receptors and are described as being useful in the treatment of allergic disorders. In the above formula $R^1$, $R^2$, $R^3$, $R^4$ and $R^5$ take various values and in particular $R^1$ is a hydrocarbyl group containing 5 to 30 carbon atoms.

The compounds of the invention have the formula

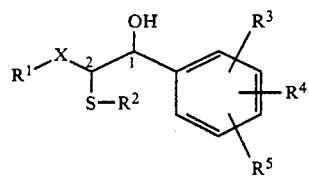

in which
$R^1$ is halo-substituted alkyl;
X is alkenylene; and $R^1$—X— contains 6 to 34 carbon atoms;
$R^2$ is $C_{1-5}$ alkyl substituted by
(i) optionally protected carboxyl, nitrile, optionally protected tetrazolyl or —CONR'R", in which R' and R" are each hydrogen or $C_{1-4}$ alkyl,

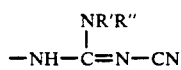

(ii)
in which R' and R" are each hydrogen or $C_{1-4}$ alkyl, or

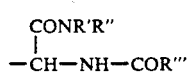

(iii)
in which R', R" and R'" are each hydrogen or $C_{1-4}$ alkyl, or
$R^2$ is a group of the formula

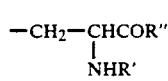

in which R' is hydrogen or an optionally protected amino acid residue, and R" is —OH or an optionally protected amino acid residue; and
$R^3$, $R^4$ and $R^5$ are each hydrogen, optionally protected carboxyl, $C_{1-4}$ alkyl, $C_{1-4}$ alkoxy, hydroxyl, optionally protected tetrazolyl, halo, trifluoromethyl, nitrile, nitro or —CONR'R" where R' and R" are each hydrogen or $C_{1-4}$ alkyl; and salts thereof.

As mentioned above, the compounds of the invention, in unprotected form, have been shown to be pharmacologically active in tests which demonstrate their antagonist effect on leukotriene receptors and indicate their use in the treatment of allergic and related disorders.

In the above general formula, $R^1$ is a halo-substituted alkyl group, for example a halo $C_{1-10}$ alkyl group. It is preferably a halo-substituted $C_{1-4}$ alkyl group. A $C_{1-4}$ alkyl group can be, for example, methyl, ethyl, propyl, isopropyl, butyl, tert. butyl and one or more, or all, of the hydrogen atoms are replaced by a halogen atom especially fluorine, chlorine or bromine. Examples of halo-substituted $C_{1-4}$ alkyl group include —$CF_3$, —$CHF_2$, —$CH_2F$, $CCl_3$, —$CHCl_2$, —$CBr_3$, —$CHBr_2$, —$CF_2Cl$, —$CFCl_2$, —$CF_2Br$, —$CFBr_2$, —$CFClBr$, —$CHFCF_3$, —$CF_2CF_3$, —$CHClCF_3$, —$CCl_2CF_3$, —$CHBrCF_3$, —$CBr_2CF_3$, —$CF_2CHF_2$, —$CF_2CH_2F$, —$CF_2CHCl_2$, —$CF_2CHCl_2$, —$CF_2CCl_3$, —$CF_2CHBr_2$, —$CHFCH_2F$, —$CHFCHF_2$, —$CH(CF_3)_2$ and —$C(CF_3)_3$. Preferred examples are groups of the formula —$CX_3$ and —$CX_2CX_3$ where each X independently is a halogen atom selected from fluorine, chlorine and bromine.

Preferably $R^1$ has at least one halogen atom on the terminal carbon atom, and preferably $R^1$ is a halo-substituted methyl group, especially trihalomethyl, such as for example, —$CF_3$, —$CCl_2F$ and —$CClF_2$, and in particular the trifluoromethyl group, —$CF_3$.

The alkenylene group X preferably contains 5 to 30 carbon atoms. More preferably X contains 6 to 20 carbon atom and especially 6 to 15 carbon atoms, and the group can be branched, though it is preferred that it is unbranched.

The X group preferably contains 2 to 4, most preferably 2, double bonds, and it is furthermore preferred that there should be a double bond in the 3,4 position of the structure shown in formula (I). Examples are of the formula

—YCH=CHCH=CH— where Y is —$(CH_2)_x$— where x is 3 to 10 or —$(CH_2)_y$CH=CH—$CH_2$—CH=CH— where y is 0 to 6. Preferably x is 7 to 10 and y is 2 to 5. Two particularly preferred values of Y are —$(CH_2)_8$— and —$(CH_2)_4$CH=CH—$CH_2$—CH=CH— corresponding to values of X of

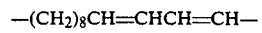

and —$(CH_2)_4$CH=CH—$CH_2$—CH=CH—CH=CH—CH=CH—

It will be appreciated that such double bonds provide opportunities for cis-trans isomeric forms. Examples of alkenylene groups are

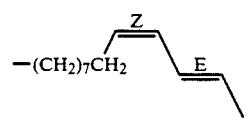

-continued and

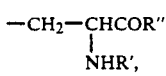 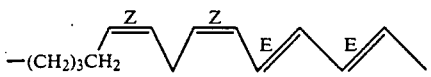

When R² is a group of the formula

—CH₂—CHCOR″
         |
         NHR′,

R′ and R″ can be derived from any of the well known amino acids linked by an amide linkage, and for example substituents such as the following are included —CH₂CH(NH₂)COOH, —CH₂CH(NH₂)CONHCH₂COOH,

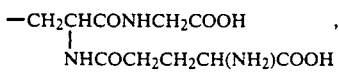

these forming with the sulphur atom to which they are attached, the cysteinyl, cysteinylglycinyl and glutathionyl radicals, respectively.

When $R^2$ is substituted $C_{1-5}$ alkyl, it is preferably of the formula —$(CH_2)_z R^6$ where z is 1 to 5, more preferably 2 to 4, though the alkylene group can be branched if desired, and $R^6$ is a substituent (i), (ii) or (iii) defined above, and is most preferably (i). It is preferred that the substituent be selected from carboxyl, nitrile, tetrazolyl or —CONR′R″ where each R′ and R″ is preferably hydrogen, methyl or ethyl. The most preferred substituents are carboxyl and tetrazolyl and particular examples of $R^2$ are —$(CH_2)_2COOH$ and

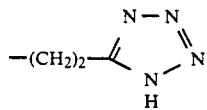

As defined above, the groups $R^3$, $R^4$ and $R^5$ can be hydrogen, optionally protected carboxyl, such as for example, carboxyl and $C_{2-5}$ alkoxycarbonyl, $C_{1-4}$ alkyl, $C_{1-4}$ alkoxy, hydroxyl, optionally protected tetrazolyl, halo, trifluoromethyl, nitrile, nitro and —CONR′R″ where each R′ and R″ are hydrogen or $C_{1-4}$ alkyl. The tetrazolyl group is preferably 1H-tetrazol-5-yl. Preferably there is a single substituent on the phenyl ring and it is preferred that the substituent he nitrile, —CONH₂, tetrazolyl or carboxyl, acid substituents such as tetrazolyl and carboxyl being best of all. Maximum biological activity is given by the compounds in which the tetrazolyl or carboxyl group is attached at the ortho or meta positions, and the most preferred groups are of the formula

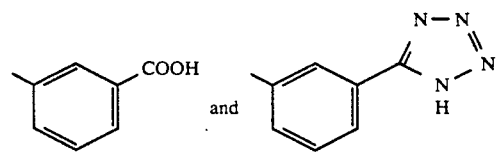

In the above general formulae $C_{1-4}$ means a straight or branched chain alkyl group, for example, methyl, ethyl, propyl, isopropyl, butyl, isobutyl and tertiary butyl, and is preferably methyl or ethyl. Similarly a $C_{1-4}$ alkoxy group is any such alkyl group attached through oxygen to the appropriate moiety, and alkoxycarbonyl is a group of the form ROCO— where R is a $C_{1-4}$ alkyl group as described above.

A particular group of compounds of formula (1) above are those of the formula

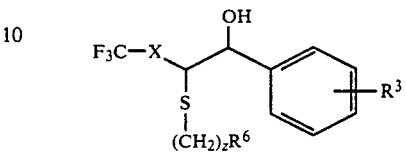

in which X is —$(CH_2)_x$—CH=CHCH=CH— where x is 6 to 10, z is 2 to 4, $R^6$ is carboxyl, nitrile, tetrazolyl or —CONR′R″ where R′ and R″ are each hydrogen or $C_{1-4}$ alkyl and $R^3$ is carboxyl, nitrile, tetrazolyl or —CONR′R″ where R′ and R″ are each hydrogen or $C_{1-4}$ alkyl. Preferably $R^3$ and $R^6$ are each carboxyl or tetrazolyl.

When substituents on the compound of formula (I) require protection during preparation they may be protected by conventional protecting groups. Compounds with such protected carboxyl, amino acid residues and tetrazolyl groups are included in the scope of the invention, though the preferred compounds with optimum biological properties are the unprotected compounds derived from them. Carboxy-protecting groups are the well known ester forming groups used for the temporary protection of acidic carboxylic acid groups. Examples of such groups which have general use are readily hydrolysable groups such as arylmethyl groups, haloalkyl groups, trialkylsilyl groups, alkyl groups, and alkenyl groups. A preferred protected carboxyl group is $C_{2-5}$ alkoxycarbonyl. Other carboxy protecting groups are those described by E. Haslam in Protective Groups in Organic Chemistry, Chapter 5. The amino-protecting groups that can be employed in the preparation of the compounds of the invention are also conventional protecting groups. Illustrative of such groups are trihaloacetyl groups especially trifluoroacetyl. Such groups are well known in the art and are discussed, for example, in Peptide Synthesis by M. Bodansky, Y. S. Klausner and M. A. Ondetti, Second Edition (1976) John Wiley & Sons. Any free hydroxy groups present in the compound of the invention may likewise be protected if needed. For example, a hydroxy group on the phenyl nucleus can be protected with a conventional labile ether forming protecting group such as an ether formed with dihydropyran or methylvinyl ether, or by esters formed with lower alkyl carboxylic acids such as formic, acetic or propionic, or such halogenated acids, for example, chloroacetic acid, dichloroacetic acid or β,β-dichloropropionic acid. Furthermore, it is usually necessary to protect any tetrazolyl group during the process of preparation, and suitable protecting groups for this purpose include the trityl and benzhydryl groups formed by reaction with the appropriate halide in the presence of base for example by reacting the tetrazolyl reactant with trityl chloride and triethylamine.

When the compound of formula (1) bears an acidic function, base addition salts can be prepared and these are to be regarded as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms together with other pharmaceutically acceptable salts are particularly preferred, but it is to be understood that other, non-pharmaceutical, salts are included in the invention since they may be useful for identification, characterisation or purification of the free compound.

When the compound of formula (1) has a basic function, acid addition salts can be prepared and these are included in the present invention. Example of such salts are those derived from, preferably non-toxic, inorganic acids such as for example hydrochloric acid, nitric acid, phosphoric acid, sulphuric acid and nitric acid, as well as salts derived from, preferably non-toxic, organic acids such as aliphatic mono- and di-carboxylic acids, phenyl-substituted alkanoic acids, hydroxy-alkanoic acids, aromatic acids, and aliphatic and aromatic sulphonic acids.

It will be appreciated that the compounds of formula (I) possess chiral centres at the carbon atoms bearing the hydroxyl and $SR^2$ groups and, accordingly, stereoisomeric forms exist R,R; S,S; R,S; and S,R, and a preferred stereospecific form is 1S,2R. Other chiral centres are also possible, depending on the nature of the various substituents, which may lead to further stereoisomeric forms. Furthermore, as mentioned above, the alkenylene moiety exhibits cis-trans isomeric forms. All such stereoisomers, and racemic mixtures thereof, are included within the scope of the invention. Isomers can be isolated from racemic mixtures by conventional methods such as by the preparation of diastereoisomers with subsequent liberation of the enantiomers or, alternatively, can be prepared by methods devised to give the pure isomer.

The invention also includes a process for producing a compound of formula (I) above, which comprises reacting a compound of the formula

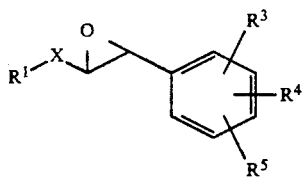

II in which $R^1$, $R^3$, $R^4$, $R^5$ and X have the above defined values, with a thiol of formula $R^2SH$, optionally followed by the removal of any protecting groups, or by interconversion of an $R^2$, $R^3$, $R^4$ or $R^5$ group.

The reaction of compound of formula (II) with thiol is preferably carried out in an organic solvent such as an alcohol, for example methanol, in the presence of a base such as a triethylamine and at a temperature of from 0° C. to 50° C. Thiol reactants containing a potential anion especially if it is sterically close to the thiol group are, desirably, protected before reaction.

It will be appreciated that it may be desired to remove any protecting groups attached to the product of the reaction. Such reactions can readily be carried out by use of a base in an inert organic solvent, such as for example, lithium hydroxide in tetrahydrofuran, or potassium carbonate in methanol, at a temperature of from 0° C. to 80° C., or by use of acid such as hydrochloric acid for removal of protecting groups from tetrazolyl, or by reduction in the case of protected amino groups, by well known procedures described for example in the authorities referred to above.

Also it will be appreciated that one or more of the substituents on the $R^1$ group or $R^3$, $R^4$ and $R^5$ groups may be interconverted, if desired. It is often preferred, depending on the nature of the group, that such interconversions are carried out after reaction of compound of formula (11) with thiol.

For example, compounds in which $R^3$, $R^4$ or $R^5$ is $C_{2-5}$ alkoxycarbonyl or in which $R^2$ bears such a group can be converted to the corresponding free carboxyl by hydrolysis by means of base in an inert organic solvent, such as for example, lithium hydroxide in tetrahydrofuran. Such methods are well known in the art. Conversely, compounds in which $R^3$, $R^4$ or $R^5$ is $C_{2-5}$ alkoxycarbonyl or $R^2$ has such a group can be prepared from the free acid by esterification of the free carboxyl group with the appropriate alcohol or by treatment with alkyl halide in the presence of base. Salts of the free acid can, of course, be prepared simply by reaction with alkali.

Compounds in which $R^3$, $R^4$ or $R^5$ is $-CONR'R''$ or in which $R^2$ bears a $-CONR'R''$ group can be prepared (i) by reacting a compound with an appropriate alkoxycarbonyl substituent with ammonia or the appropriate amine of formula $R'R''NH$, (ii) by the reaction of an amine of formula $R'R''NH$ with the appropriate acyl chloride, which can in its turn be derived from the free carboxyl derivative by the reaction of thionyl chloride, or (iii) by reacting the acid derivative with a suitable amine in the presence of a carbodiimide. Such reactions are well known in the art.

Compounds in which $R^3$, $R^4$ or $R^5$ is a nitrile group or $R^2$ has such a group can be prepared by dehydration of the appropriate amide ($-CONH_2$), using a convenient dehydrating agent such as for example, a mixture of triphenylphosphine and carbon tetrachloride.

Compounds in which $R^3$, $R^4$ or $R^5$ is tetrazolyl or $R^2$ has such a group can be prepared by reaction of the cyano derivative prepared as above with, for example tributyl tin azide or sodium azide and ammonium chloride in dimethylformamide. Salts can be prepared from the tetrazolyl derivatives by the addition of base according to standard techniques.

It will be appreciated that the steps of removal of protecting group or interconversion of groups, can be carried out in whatever sequence best suits convenience and the aim of maximising yield.

The reactants of formula $R^2SH$ are known compounds (see for example British Patent 2 144 422 and European Patent Publication 0 298 583), or they can be prepared by methods of well known in the art. When they bear amino or carboxyl groups the reaction may benefit in yield if these groups are first protected, but such initial protection is by no means necessary in all cases.

Compounds of formula (II), and salts thereof, are novel and are included as part of the present invention. They may be prepared by the Wittig reaction of a phosphonium salt of formula $R'-X'-CH_2P^+Ph_3Br^-$, $X'$ being an appropriate alkylene or alkenylene group, in the presence of a base such as butyl lithium, with an aldehyde of formula (III) or (IV)

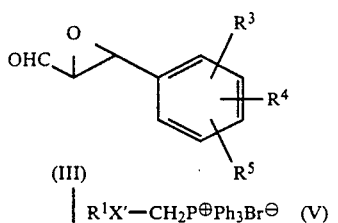
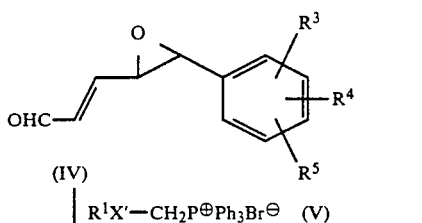

The reaction is generally carried out in an inert organic solvent such as for example, tetrahydrofuran, at a temperature of from −110° C. to 0° C.

Compounds of formula (III) are known intermediates (see for example British Patent 2144422) and can be prepared by two principal routes. Firstly, they may be prepared, as racemic mixtures, by oxidation with, for example, hydrogen peroxide and sodium hydrogen carbonate in methanolic solution, of an aldehyde of the formula

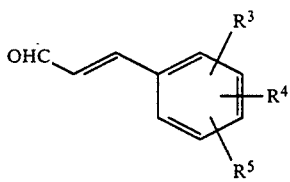

In its turn, the aldehyde of formula (III) may be converted to one of formula (IV) by reaction with formylmethylenetriphenylphosphorane.

Alternatively, the compounds of formula (III) may be prepared by oxidation of an epoxy alcohol of the formula

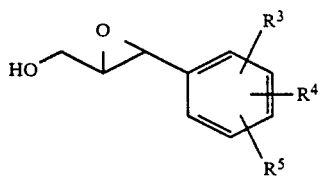

with an oxidising agent such as, for example, chromium trioxide in pyridine, or dimethylsulphoxide and oxalyl chloride in dichloromethane. Compounds of formula (VI) can be prepared in stereospecific form and since the steric configuration is retained on oxidation to provide the aldehyde of formulae (III) and, ultimately, of formula (IV), this route can be employed to provide stereospecific compounds of formula (I).

Compounds of formula (VI) are prepared from the allyl alcohol

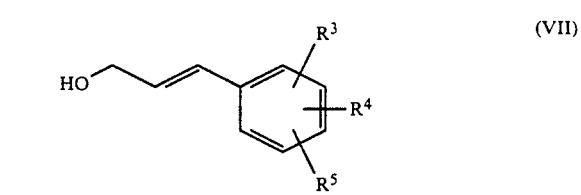

using as epoxidising agent a reagent such as titanium isopropoxide and t-butyl hydroperoxide in the presence of L or D dialkyl tartrate which yields the S,S or R,R epoxide with the above E olefin. When the Z olefin is used as starting material, the appropriate S,R and R,S stereoisomers result. Compounds of formula (VII) can be prepared from the appropriate benzaldehyde via a sequence of reactions involving reaction with malonic acid to provide the cinnamic acid derivative, treatment with oxalyl chloride to give the acid chloride, and reduction with a reagent such as lithium tri-t-butoxyaluminohydride.

Compounds of formula (V) can be synthesised from the appropriate halide, for example $R^1X'$—$CH_2Br$, by reaction with triphenylphosphine. The halide reactant can be synthesised by use of a copper-catalysed Grignard coupling reaction.

The following scheme gives examples of the way in which preferred compounds of the invention may be prepared:

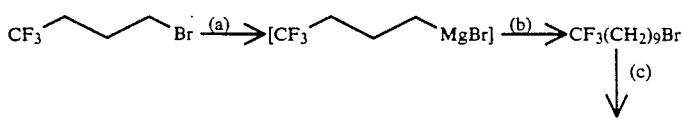

-continued

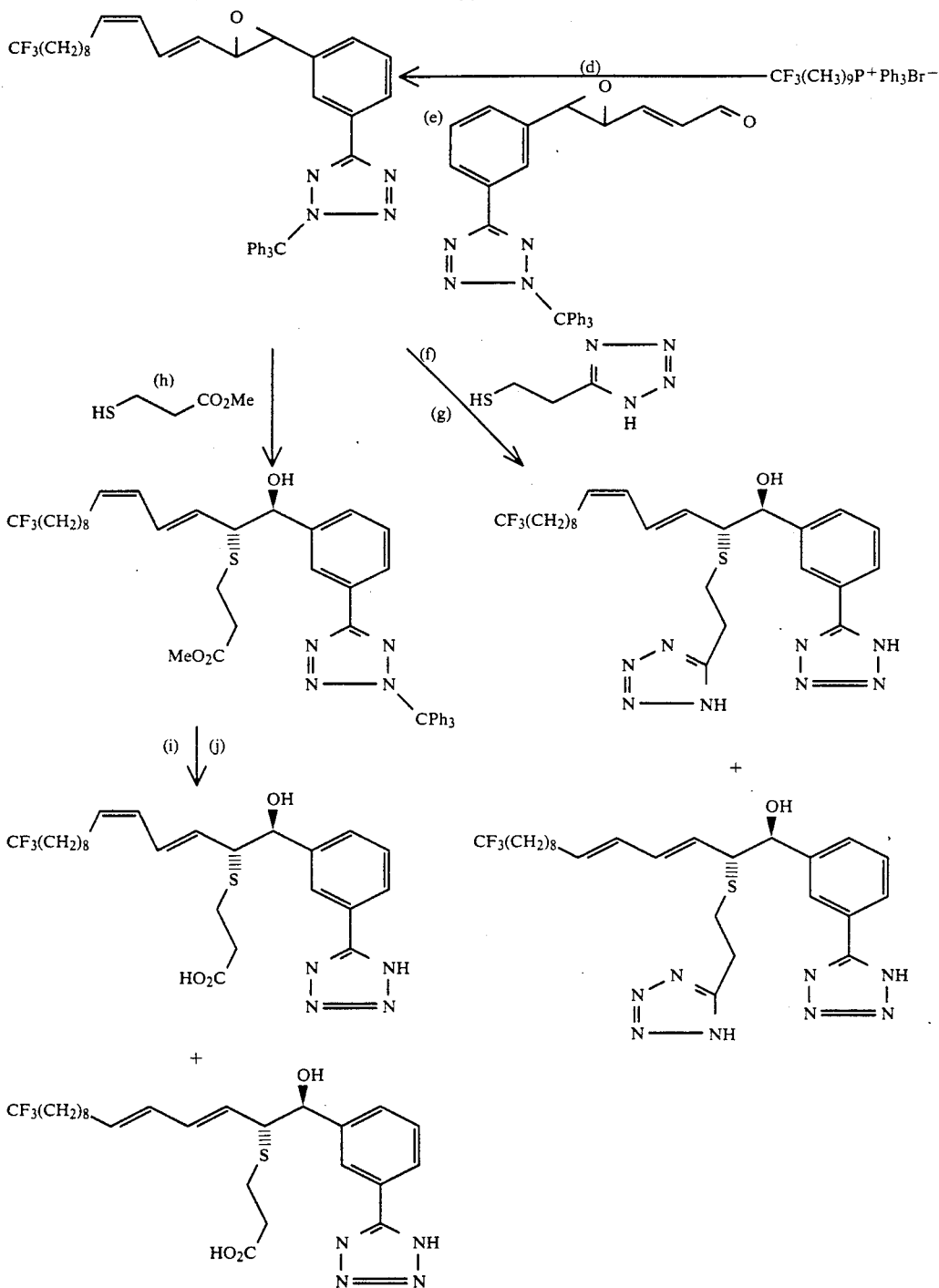

Key:
(a) magnesium
(b) dibromohexane, lithium chloride and cuprous chloride
(c) triphenylphosphine
(d) sodium bistrimethylsilyl amide
(e) epoxide of formula (IV)
(f) thiol of formula $R^2SH$ and potassium t-butoxide
(g) acid (formic acid)
(h) thiol of formula $R^2SH$ and triethylamine
(i) acid (formic acid)
(j) base (potassium carbonate)

The compounds of the present invention are pharmacologically active being leukotriene antagonists. This is shown by the in vitro test on guinea pig ileum segments at concentrations of from 10 ng to 50 μg per ml, according to the method of Schild (1947) Brit. J. Pharm. 2, 197-206 (the unprotected compounds of formula (I) described in the following Examples exhibited an $IC_{50}$ against $LTD_4$ of less than $10^5$—molar). Also compounds of the invention are active in the in vivo Guinea pig Pulmonary Function Test of Austen and Drazen (1974) J. Clin. Invest. 53 1679–1685 at intravenous dosage levels of from 0.05 μg to 5.0 mg/kg and in a modified "Herxheimer" test (Journal of Physiology (London) 117, 251 (1952)) at doses of from 25 to 200 mg/kg. The "Herxheimer" test is based on an $LTD_4-$ induced bronchospasm in guinea pigs which closely resembles an asthmatic attack in man.

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and adult respiratory distress syndrome, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds of the invention also have potential in the treatment of cardiovascular disease such as septic shock and ischaemic heart diseases for example coronary artery disease and myocardial infarction, cerebrovascular diseases, renal and hepatic diseases for example renal ischaemia and hepatorenal syndrome, as shown by their activity in the test described by Shipley R. E. and Tilden J. H. Proc.Soc. exp. Biol.Med. 64, 453–455 (1947).

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection or infusion, and especially by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers. For administration parenterally forms of presentation include injectible solutions and suspensions, and infusions. Such formulations may preferably comprise a complexing agent for example a modified starch such as β-cyclodextrin or a protein such as human serum albumin, or a lecithin.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patent.

Where the compositions are formulated in unit dosage form, it is preferred that each unit dosage form contains from 1 mg to 500 mg, for example, from 5 mg to 100 mg of active material. The term "unit dosage form" refers to physically discrete units suitable as unit dosages for human subjects and animals, each unit containing a predetermined quantity of active material calculated to produce the desired therapeutic effect, in association with the required pharmaceutical carrier. Alternatively as mentioned above the formulation may be in the form of an injectible solution or suspension, or an infusion, in which case it preferably contains from 1 to 50 mg/ml of active material.

The active compounds are effective over a wide dosage range and, for example, dosages per day will normally fall within the range of from 0.001 or 0.01 to 50 mg./kg, more usually in the range of from 0.05 to 10 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples.

EXAMPLE 1

(1S,2R)-5-[3-(2-{2-Carboxyethylthio}-1-hydroxy-15,15,15-tri-fluoropentadeca-3(E)5(Z)-dienyl)phenyl]-1H-tetrazole

(1)(i) 1-Bromo-10,10,10,-trifluorodecane

A solution of 1-bromo-4,4,4,-trifluorobutane (4.75 g) in dry tetrahydrofuran (20 ml) was added slowly to a stirred suspension of magnesium turnings (1.2 g) in tetrahydrofuran (15 ml) at 40° C. under nitrogen, adding a small crystal of iodine to initiate the reaction. The mixture was stirred for a further 20 minutes at 40° C. then the clear solution was decanted from the excess magnesium and added dropwise over 1 hour to a stirred solution of 1,6-dibromohexane (6.0 g), anhydrous lithium chloride (30 mg) and anhydrous copper (I) chloride (50 mg) in dry tetrahydrofuran (50 ml) at 0–5° C. under nitrogen. The solution was stirred for a further 2 hours without cooling, then poured onto ice-dilute hydrochloric acid and extracted with ether. The extract was washed with brine, dried and evaporated and the residual oil was chromatographed on a silica column, eluting with hexane to give the product as a colourless oil, b.p. 47–48° C./0.05 mm of Hg.

(ii) 10,10,10-Trifluorodecyl-triphenylphosphonium bromide

A stirred solution of 1-bromo-10,10,10-trifluorodecane (4.75 g) and triphenylphosphine (4.53 g) in acetonitrile (100 ml) was heated under reflux for 3 days. The solution was evaporated under vacuum and the residue was washed with ether, dissolved in toluene and the solution diluted with ether to give the product as a hygroscopic solid.

(2)(i) 3-Cyanocinnamoyl chloride

3-Cyanocinnamic acid (200 g) was treated with diethyl ether (3333 ml), oxalyl chloride (100.8 ml) and dimethyl formamide (2 ml) and stirred at room temperature for 5.5 hours in a vessel closed by a silica tube. The solution was decanted from insoluble material and evaporated to dryness to leave a pale yellow to white solid, which was dried at 40–50°/high vacuum to give the acid chloride, melting point 105° C.

(ii) (3-Hydroxy-1-propenyl)benzonitrile $NaBH_4$—$Al_2O_3$ (1219 g) (prepared according to Santaniello, Ponti and Manzocchi, "Synthesis", 1978, 891, but using Woelm Alumina N instead of the type specified; the reagent formed contained 2.04 Mmole of $NaBH_4$ per gram) was stirred in diethyl ether (6340 ml) at room temperature and the acid chloride (200 g) from (3)(i) in ether (7800 ml) was added dropwise during one hour. The temperature rose from 20° to 27°, and had fallen to 26° one hour after completion of the addition. The mixture was stirred for a total of 1.5 hours after completion of the acid chloride addition. The alumina was filtered off and washed with ether (3×2 l), the filtrate was evaporated to dryness to leave an oil which solidified on storage in a refrigerator. The solid alcohol had a melting point <50° C.

(iii) 3-(5-Tetrazolyl)cinnamyl alcohol

3-Cynacinnamyl alcohol (292.97 g), dimethylformamide (914 ml), triethylamine hydrochloride (558.7 g) and sodium azide (358.85 g) were added to a flask. The reaction was carried out under nitrogen and after addition of all the reactants heat was applied. The temperature of the reaction mixture reached 100° C. 1-2 hours after commencement of heating and the solution was stirred and heated at 100° for 8 hours. The solution was transferred to a 10 litre flask, treated with water (2944 ml), stirred and cooled to 10° C. (ice-bath), treated with concentrated HCl (736 ml) and stirred for 2.5 hours while the temperature dropped from 20° to 5° C. The solid was filtered washed with cold water (3×2 l and 1×1 l) and dried, initially for 1.5 hours in a fluid-bed drier, then at 60°/high vacuum to give 3-(5-tetrazolyl)-cinnamyl alcohol, melting point 174° C.

(iv) (E) 3-[3-(2-Triphenylmethyl-2H-tetrazol-5-yl)phenyl]-2-propenol

To a solution of 3-[3-(1H-tetrazol-5-yl)phenyl]-2-propenol of (iii) above (2.02 g) in dry dichloromethane (50 ml) was added triethylamine (1.5 ml) followed by triphenylchloromethane (2.8 g) in dry dichloromethane. The solution was stirred at room temperature for 90 minutes, washed with water (50 ml), followed by sodium bicarbonate solution (5%; 50 ml), dried over magnesium sulphate, filtered and evaporated under reduced pressure to give a pale brown viscous oil which crystallised on standing to a cream solid.

(v) (2S,3S)-3-[3-(2-Triphenylmethyl-2H-tetrazol-5-yl)-phenyl]-2,3-epoxypropanol.

L-(+)-Dimethyl tartrate (1.85 g) was added in dry dichloromethane (10 ml) dropwise to a stirred solution of titanium (IV) isopropoxide (3.1 ml) in dry dichloromethane (30 ml) at −20° to −25° C. under nitrogen. The solution was stirred for 10 minutes and a solution of 3-[3-(2-triphenylmethyl-2H-tetrazol-5-yl)phenyl]-2-propenol (4.5 g) in dry dichloromethane (20 ml) was added, followed by a 3.7M solution of t-butylhydroperoxide in toluene (6.7 ml), both at −20° to −25° C. The pale orange solution was left to stand in a freezer for 3 hours. To the stirred solution was added aqueous tartaric acid (10%; 50 ml) and the mixture stirred for 1 hour, filtered and separated. The dichloromethane layer was dried over magnesium sulphate filtered and evaporated under reduced pressure to give a yellow oil. The oil was dissolved in carbon tetrachloride, washed with water, dried over magnesium sulphate, filtered and evaporated under reduced pressure to give a pale yellow oil. The oil was chromatographed on a silica gel column using diethyl ether and hexane (2:1) and the required fractions evaporated under reduced pressure to give a colourless crystalline solid.

(vi) (1S,2S)-5-[3-(1,2-Oxido-5-oxopent-3(E)-enyl)phenyl]-2-trityl-2H-tetrazole.

A solution of dry dimethylsulphoxide (8.9 ml) in dry dichloromethane (25 ml) was added over 12 minutes to a stirred solution of oxalyl chloride (5.2 ml) in dichloromethane (100 ml) at −60° C. under nitrogen. The solution was stirred for a further 5 minutes at −60° C. then a solution of compound of step (v) above (23 g) in dichloromethane (100 ml) was added over 20 minutes. The mixture was stirred for a further 15 minutes at −60° C. then triethylamine (18 ml) was added over 10 minutes. The mixture was allowed to warm to room temperature, solid triphenylphosphoranylideneacetaldehyde (13 g, 42.8 mmol) was added and the mixture was stirred for 16 hours and then evaporated. The residue was extracted with ether (3×250 ml), the extract was evaporated and the residue chromatographed on a silica column eluting with ether:hexane (3:1) to give the product as a pale solid.

(vii) (1S,2S)-5-[3-(1,2-Oxido-15,15,15-trifluoropentadeca-3(E),5(Z)-dienyl)-phenyl]-2trityl-2H-tetrazole A 1M solution of sodium bis(trimethylsilyl) amide in tetrahydrofuran (7.7 ml) was added dropwise to a stirred solution of 10,10,10-trifluorodecyl-triphenylphosphonium bromide (4.0 g) in tetrahydrofuran (10 ml). The orange mixture was stirred for 40 minutes then cooled to −90° to −100° C. and a solution of (1S,2S)-5-[3(1,2-oxido-5-oxopent-3(E)-enyl)phenyl]-2-trityl-2H-tetrazole (3.6 g) in tetrahydrofuran (10 ml) was added dropwise. The mixture was stirred for a further 40 minutes at −80° to −90° C., warmed to room temperature and evaporated. The residue was extracted with ether and the extract was evaporated. Chromatography of the residue on a silica column eluting with ether:hexane (1:2) gave the product as a clear gum.

(3)(i) (1S,2R)-5-[3-(1-Hydroxy-2-{2-methoxycarbonylethylthio}-15, 15,15-trifluoropentadeca-3(E)5(Z)-dienyl)phenyl]-2-trityl-2H-tetrazole A solution of (1S,2S)-5-[3-(1,2-oxido-15, 15,15-trifluoropentadeca-3(E)5(Z)-dienyl)phenyl]-2-trityl-2H-tetrazole (2.0 g), methyl 3-mercapto-propionate (0.5 ml)

and triethylamine (3 ml) in methanol (30 ml) was stirred under nitrogen for 16 hours. The solution was evaporated and the residue was chromatographed on a silica column eluting with ether:hexane (1:1) to give the product as a colourless oil.

NMR (300 MHz, CDCl$_3$) δ; 1.2–1.6 (12p), 2.0–2.2 (4p, —CH$_2$CF$_3$ and —CH$_2$—CH=), 2.6, 2.8 (2p, 2p, —CH$_2$CH$_2$S), 3.64 (3p, CO$_2$Me), 3.68 (1p, CHS), 4.83 (1p, CHO), 5.6, 6.4 (1p, 1p, —CH=CH—, trans), 5.4, 6.0 (1p, 1p, —CH=CH—, cis), 7.1–7.5, 8.1 (19p, Ar).

(ii) (1S, 2R)-5-[3-(2-{2-Carboxyethylthio}-1-hydroxy-15, 15,15-trifluoropentadeca-3(E)5(Z)-dienyl)phenyl]-1H-tetrazole A solution of (1S,2R)-5-[3-(1-hydroxy-2-2-methoxycarbonylethylthio}-15, 15,15-trifluoropentadeca-3(E)5(Z)-dienyl)-phenyl]-2-trityl-2H-tetrazole (2.5 g, 3.2 mmol) in ether (50 ml) was diluted with 50% formic acid (50 ml) and the mixture was stirred for 4 hours then evaporated. A solution of the residue in methanol (150 ml) was diluted with 0.5M potassium carbonate solution (150 ml) and the mixture was stirred for 16 hours and concentrated to a 120 ml. This mixture was washed with ether, acidified and extracted with ether. The ether extract was dried and evaporated and the residue was purified by reverse-phase high-pressure liquid chromatography (RP-HPLC) on a C18-capped silica column eluting with methanol:water: acetic acid (75:25:0.1) to give the major product as a gummy solid which crystallised from ether-hexane.

NMR (300 MHz, CD$_3$OD) δ; 1.2–1.6 (12p), 2.0–2.2 (4p, —CH$_2$CF$_3$ and —CH$_2$CH=), 2.52, 2.67 (2p, 2p, —CH$_2$CH$_2$S), 3.7 (1p, CHS), 4.85 (1p, CHO), 5.45, 6.3 (1p, 1p, —CH=CH—, trans), 5.35, 5.96 (1p, 1p, —CH=CH—, cis), 7.55, 7.95, 8.05 (4p, Ar).

EXAMPLE 2

(1S,2R)-5-[3-(2-{2-Carboxyethylthio}-1-hydroxy-15, 15,15-tri-fluoropentadeca-3(E)5(E)-dienyl)phenyl]-1H-tetrazole The compound was isolated by RP-HPLC as a minor product from the reactions described in Example 1.

NMR (300 MHz, CH$_3$OD) δ; 1.3–1.6 (12p), 2.0–2.2 (4p, —CH$_2$CF$_3$ and —CH$_2$CH=), 2.5, 2.66 (2p, 2p, —CH=CH—CH=CH—), 7.5–7.9, 8.11 (40, Ar).

EXAMPLE 3

(1S,2R)-5-[3-(1-Hydroxy-2-{2-1H-tetrazol-5-ylethylthio}-15, 15,15-trifluoropentadeca-3(E)5(Z)-dienyl)phenyl]-1H-tetrazole (1)(i) 3-(Benzylthio)-propionitrile Acrylonitrile (21.4 g) was added dropwise to a solution of benzyl mercaptan (49.6 g) and triethylamine (4 ml) in methanol (400 ml). This addition lead to an exothermic reaction and the temperature of the reaction mixture was allowed to rise from room temperature to 35° C. After 10 minutes the reaction was almost complete as shown by TLC, there being a trace of unreacted thiol still present. Additional acrylonitrile (0.5 g) was then added to consume the last of the thiol. After a further 10 minutes the solution was evaporated to give the title compound 69.0 g as a pale yellow oil.

(ii) 5-[2-(Benzylthio)-ethyl]-1H-tetrazole

A mixture of 3-(benzylthio)-propionitrile (33.30 g), sodium azide (61.14 g) and ammonium chloride (50.33 g) in dry dimethylformamide (220 ml) was stirred at 120° for 20 hours. Additional sodium azide (24.50 g) and ammonium chloride (20.13 g) was then added, and heating at 120° continued for further 6 hours.

The cooled reaction mixture was poured into a mixture of ice/water and 2 molar hydrochloric acid and extracted with dichloromethane. The organic extracts were in turn extracted with ten per cent sodium carbonate solution, and the basic extracts cautiously acidified with concentrated hydrochloric acid. The resulting precipitate was collected by filtration, washed with water, and dried in vacuo to give the required product as a white solid, m.p. 80°–82° C.

(iii) 5-(2-Mercaptoethyl)-1H-tetrazole

5-[2-Benzylthio-ethyl]-1H-tetrazole (15.00 g) was added portionwise as a solid to a solution of sodium metal (7.84 g) in liquid ammonia (200–300 mls). The reaction mixture was stirred at 20° under a drying tube (silica gel) for 2 hours and then very cautiously quenched with methanol (100 ml). The excess ammonia was removed under a nitrogen stream and the residue acidified with hydrochloric acid and extracted with ethyl acetate. The organic extracts were dried over magnesium sulphate, filtered and evaporated under reduced pressure to yield the title compound as a white solid (7.15 g), m.p. 104°–106° C.

(2) (1S,2R)-5-[3-(1-Hydroxy-2-{ 2-1H-tetrazol-5-ylethyl-thio}-15, 15,15-trifluoropentadeca-3(E)5(Z)-dienyl)phenyl]-H-tetrazole A stirred mixture of (1S,2S)-5-[3-(1,2-oxido-15,15,15-trifluoropentadeca-3(E)5(Z)-dienyl)phenyl]-2-trityl-2H-tetrazole (Example 1 (2)(vii), 0.5 g) 5-(2 -mercaptoethyl)-1H-tetrazole (0.20 g) and potassium t-butoxide (0.42 g) in t-butanol (10 ml) was heated at 35° C. under nitrogen for 4 hours. The mixture was poured onto ice-hydrochloric acid and extracted with ether. The extract was evaporated and a solution of the residue in ether (20 ml) and 50% formic acid (20 ml) was stirred for 6 hours then evaporated. A solution of the residue in ether was extracted with dilute sodium carbonate solution, the aqueous extract was immediately acidified and re-extracted with ether. This ether extract was dried and evaporated and the residue was purified by RP-HPLC (C-18 silica, methanol:water:acetic acid—70:30:0.1) to give the product as a sticky solid.

NMR (300 MHz, CD$_3$OD), δ; 1.1–1.6 (12p), 2.0–2.2 (4p, —CH$_2$CF$_3$ and —CH$_2$CH=), 2.87, 3.19 (2p, 2p, —CH$_2$CH$_2$S), 3.60 (1p, CHS), 4.87 (1p, CHO), 5.6, 6.2 (1p, 1p, —CH=CH—, trans), 5.35, 5.9 (1p, 1p, —CH= CH—, cis), 7.5–7.9, 8.0 (4p, Ar).

EXAMPLE 4

(1S,2R)-5-[3-(2-{2-Carboxyethylthio}-1-hydroxy-17, 17,17-trifluoroheptadeca-3(E)5(Z)-dienyl)phenyl]-1H-tetrazole This compound was prepared as described in Example 1 using the appropriate dibromoalkane in step 1(i).

NMR (300 MHz, CH$_3$OD) δ; 1.2–1.6 (16p), 2.0–2.2 (4p, —CH$_2$CF$_3$ and —CH$_2$CH=), 2.52, 2.66 (2p, 2p, —CH$_2$CH$_2$S), 3.67 (1p, CHS), 4.9 (1p CHO), 5.45, 6.30 (1p, 1p, —CH=CH—, trans), 5.35, 5.96 (1p, 1p, —CH=CH—, cis), 7.54, 7.91, 8.01 (4p, Ar).

EXAMPLE 5

(1S,2R)-5-[3-(2-{2-Carboxymethylthio}-1-hydroxy-13, 13,13-trifluorotrideca-3(E)5(Z)-dienyl)phenyl}-1H-tetrazole This compound was prepared as described in Example 1 using the appropriate dibromoalkane in step 1(i).

NMR (300 MHz, CD$_3$OD) δ; 1.2-1.6 (8p) 2.0-2.2 (4p, —CH$_2$CF$_3$, and —CH$_2$CH=), 2.50, 2.55 (2p,2p, —CH$_2$CH$_2$S), 3.70 (1p CHS), 5.65, 6.25 (1p, 1p, —CH=CH—, trans), 5.35, 5.98 (1p, 1p, —CH=CH—, cis), 7.55, 7.95, 8.02 (4p, Ar).

EXAMPLE 6

(1S,2R)-5-[3-(2-{2-Carboxyethylthio}-1-hyroxy-7-{perfluorooctyl} hepta-3(E)5(Z)-dienyl)phenyl]1H-tetrazole

This compound was prepared as described in Example 1 using 1H,1H,2H,2H-perfluorodecyl iodide (available from Fluorochem Limited) in step 1(ii).

NMR (300 MHz, CD$_3$OD) δ; 2.50, 2.65 (2p,2p, —CH$_2$CH$_2$S) 3.04 (2p, C$_8$F$_{17}$CH$_2$—) 5.35, 6.29 (1p, 1p, —CH=CH—, cis) 5.87, 6.33 (1p,1p, —CH=CH—, trans) 7.3, 7.90, 7.99 (4p, Ar).

EXAMPLE 7

Soft gelatin capsule

Each soft gelatin capsule contains:

| Active ingredient | 150 mg |
|---|---|
| Arachis oil | 150 mg |

After mixing together, the blend is filled into soft geleatin capsules using the appropriate equipment.

EXAMPLE 8

Hard gelatin capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 9

Aerosol

| Active ingredient | 10 mg |
|---|---|
| Ethanol | 50 mg |
| Dichlorodifluoromethane (Propellant 12) | 658 mg |

| -continued | |
|---|---|
| Dichlorotetrafluorothane (Propelant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 μl equivalent to 0.5-1 mg active ingredient.

We claim:

1. A compound of the formula

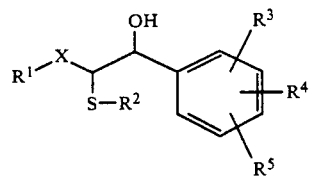

in which
R$^1$ is halo-substituted C$_1$-C$_{10}$ alkyl;
X is C$_5$-C$_{30}$ alkenylene;
R$^2$ is C$_{1-5}$ alkyl substituted by —COOH or 5-tetrazolyl;
R$^4$ and R$^5$ are each hydrogen
and R$^3$ is —COOH or 5-tetrazolyl; and pharmaceutically acceptable salts thereof.

2. A compound according to claim 1 in which R$^1$ is halo-substituted C$_{1-4}$ alkyl.

3. A compound according to claim 2 in which R$^1$ has at least one halogen atom on the terminal carbon atom.

4. A compound according to claim 2 in which X is alkenylene containing 6 to 15 carbon atoms and 2 to 4 double bonds.

5. A compound according to claim 1 of the formula

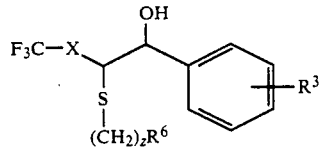

in which X is —(CH$_2$)$_x$—CH=CHCH=CH— where x is 6 to 10, z is 2 to 4, and R$^6$ is —COOH or 5-tetrazolyl, or a pharmaceutically acceptable salt thereof.

6. (1S,2R)-5-[3-(1-Hydroxy-2-{2-1H-tetrazol-5-ylethylthio}-15, 15,15-trifluoropentadeca-3(E)5(Z)-dienyl)phenyl}-1H-tetrazole.

7. A pharmaceutical formulation comprising a compound according to claim 1, in unprotected form, together with a pharmaceutically-acceptable diluent or carrier therefor.

8. A method of treating an animal, including a human, suffering from or susceptible to an allergic or cardiovascular disorder, which comprises administering an effective amount of an unprotected compound of formula (I) as defined in claim 1, or a pharmaceutically-acceptable salt thereof.

* * * * *